United States Patent
Yazaki et al.

(10) Patent No.: US 6,586,420 B1
(45) Date of Patent: Jul. 1, 2003

(54) QUINOLINECARBOXYLIC ACID DERIVATIVE OR ITS SALT

(75) Inventors: Akira Yazaki, Takata-gun (JP); Yoshiko Niino, Takata-gun (JP); Yasuhiro Kuramoto, Takata-gun (JP); Yuzo Hirao, Takata-gun (JP); Yoshihiro Oshita, Takata-gun (JP); Norihiro Hayashi, Takata-gun (JP); Hirotaka Amano, Takata-gun (JP)

(73) Assignee: Wakunaga Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/069,514

(22) PCT Filed: Sep. 1, 2000

(86) PCT No.: PCT/JP00/05962
§ 371 (c)(1),
(2), (4) Date: Mar. 4, 2002

(87) PCT Pub. No.: WO01/17991
PCT Pub. Date: Mar. 15, 2001

(30) Foreign Application Priority Data

Sep. 2, 1999 (JP) .......................................... 11/248684

(51) Int. Cl.[7] ........................ A61K 31/55; A61K 31/47; C07D 215/16
(52) U.S. Cl. ................... 514/210.21; 514/312; 546/156
(58) Field of Search ............................ 514/210.21, 312; 546/156

(56) References Cited

U.S. PATENT DOCUMENTS 5,998,436 A * 12/1999 Yazaki et al. ............... 514/300

FOREIGN PATENT DOCUMENTS

| EP | 0 787 720 A1 | 8/1997 |
|----|----|----|
| EP | 0 911 327 A1 | 4/1999 |
| EP | 1 193 266 A1 | 4/2002 |
| JP | 53-141286 | 12/1978 |
| JP | 55-031042 | 3/1980 |
| JP | 57-046986 | 3/1982 |
| JP | 58-074667 | 5/1983 |
| JP | 60-228479 | 11/1985 |
| JP | 11292873 | 10/1999 |
| WO | WO 97/11068 | 3/1997 |
| WO | WO 01/02390 A1 | 1/2001 |

OTHER PUBLICATIONS

CA 126:305587, abstract of Yazaki, WO 9711068, 1997.*

* cited by examiner

*Primary Examiner*—D. Margaret Seaman
(74) *Attorney, Agent, or Firm*—Oblon, Spivak, McClelland, Maier & Neustadt, P.C.

(57) ABSTRACT

The present invention relates a 1-(6-amino-3,5-difluoropyridin-2-yl)-6-fluoro-7-(3-hydroxyazetidin-1-yl)-8-methyl-1,4-dihydro-4-oxoquinoline-3-carboxylic acid or salt thereof; and drugs containing the same as the active ingredient. Since this compound or salt thereof is highly stable to light while sustaining the excellent properties inherent to quinolone antibacterial agents, an antibacterial agent comprising, as an active ingredient, the invention compound or salt thereof can be stored over a long period of time without suffering from any decrease in the drug effect and can therefore be supplied as stable preparations such as injections, eye drops and surgical medicines.

15 Claims, 3 Drawing Sheets

QUINOLINECARBOXYLIC ACID DERIVATIVE OR ITS SALT

TECHNICAL FIELD

The present invention relates to quinolinecarboxylic acid derivatives or salts thereof having excellent antibacterial action and photostability, and antibacterial agents containing the same.

BACKGROUND ART

Since compounds having quinolinecarboxylic acid as a basic skeleton are excellent in antimicrobial activity and broad antibacterial spectrum, a number of useful ones as synthetic antibacterial agents are known. Among them, norfloxacin (Japanese Patent Application Laid-Open No. Sho 53-141286), enoxacin (Japanese Patent Application Laid-Open No. Sho 55-31042), ofloxacin (Japanese Patent Application Laid-Open No. Sho 57-46986), ciprofloxacin (Japanese Patent Application Laid-Open No. Sho 58-74667), tosufloxacin (Japanese Patent Application Laid-Open No. Sho 60-228479) and the like have wide clinical utility as therapeutic agents for infectious diseases.

These compounds are, however, still insufficient in antimicrobial activity, intestinal absorption and metabolic stability, and in addition, they are known to cause cytotoxicity or photodermatosis. Thus, many problems remain unsolved.

It is reported that some quinolinecarboxylic acid compounds are not stable to light and happen to be colored or decomposed when exposed to light. Consideration must be taken for some of their dosage forms so as to pharmaceutically overcome this drawback.

DISCLOSURE OF THE INVENTION

An object of the present invention is therefore to provide a compound which has reduced side effects, is excellent in antimicrobial activity, intestinal absorption and metabolic stability and is optically stable.

Under such circumstances, the present inventors found that pyridonecarboxylic acid derivatives each represented by the following formula (I):

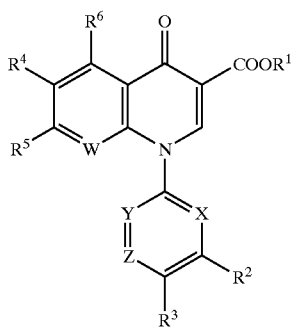

(I)

[wherein $R^1$ represents a hydrogen atom or a carboxyl protective group; $R^2$ represents a hydroxyl group, a lower alkoxy group, or a substituted or unsubstituted amino group; $R^3$ represents a hydrogen atom or a halogen atom; $R^4$ represents a hydrogen atom or a halogen atom; $R^5$ represents a halogen atom or an optionally substituted saturated cyclic amino group; $R^6$ represents a hydrogen atom, a halogen atom, a nitro group, or an optionally protected amino group; X, Y and Z may be the same or different and respectively represent a nitrogen atom, —CH= or —CR$^7$= (wherein $R^7$ represents a lower alkyl group, a halogen atom, or a cyano group) (with the proviso that at least one of X, Y and Z represents the nitrogen atom), and W represents a nitrogen atom or —CR$^8$= (wherein $R^8$ represents a hydrogen atom, a halogen atom, or a lower alkyl group)], or salts thereof have excellent antibacterial properties against both gram negative and gram positive bacteria and have a markedly low toxicity so that they are useful as a synthetic antibacterial agent, and already filed an international application (WO97/11068) for it.

The present inventors have proceeded with a further investigation on photostability. As a result, it has been found that among the above-described pyridonecarboxylic acid derivatives (I), 1-(6-amino-3,5-difluoropyridin-2-yl)-6-fluoro-7-(3-hydroxyazetidin-1-yl)-8-methyl-1,4-dihydro-4-oxoquinoline-3-carboxylic acid (Compound 1) of the following formula:

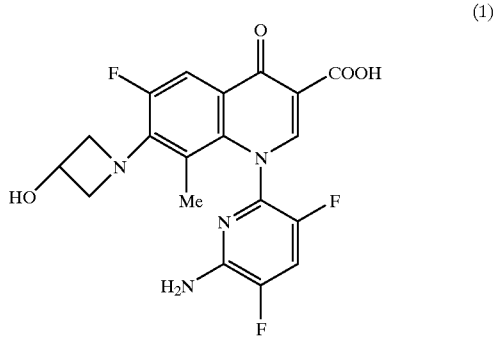

(1)

which has a 6-amino-3,5-difluoropyridinyl group on position 1, a hydroxyazetidinyl group on position 7 and a methyl group on position 8, or salt thereof has markedly high photostability so as to permit formulation into any dosage form as a preventive or remedy of various infectious diseases, while sustaining strong antimicrobial activity and low toxicity inherent to the pyridonecarboxylic acid derivatives of the formula (I), leading to the completion of the invention.

In the present invention, there is thus provided 1-(6-amino-3,5-difluoropyridin-2-yl)-6-fluoro-7-(3-hydroxyazetidin-1-yl)-8-methyl-1,4-dihydro-4-oxoquinoline-3-carboxylic acid or salt thereof.

In the present invention, there is also provided a drug comprising said compound or salt thereof as an active ingredient.

In the present invention, there is also provided a pharmaceutical composition comprising said compound or salt thereof and a pharmaceutically acceptable carrier.

In the present invention, there is also provided the use of said compound or salt thereof for the preparation of a drug.

Furthermore, in the present invention, there is also provided a method for treating infectious diseases, characterized by administering said compound or salt thereof.

BEST MODE FOR CARRYING OUT THE INVENTION

The compound according to the present invention has a 6-amino-3,5-difluoropyridinyl group on position 1, a hydroxyazetidinyl group on position 7 and a methyl group on position 8, each of quinolinecarboxylic acid.

Figure 2:
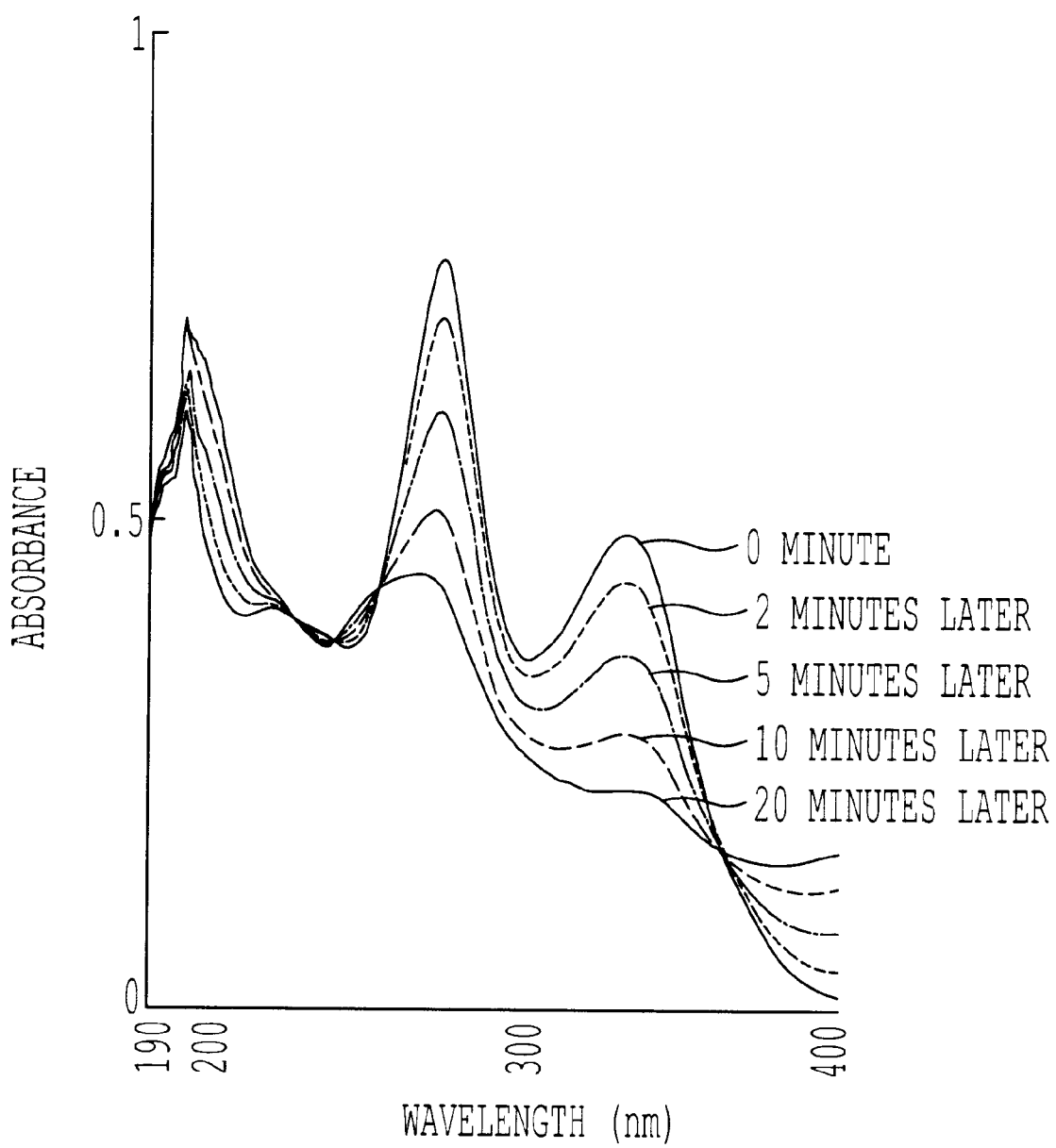
FIG. 2 shows a time-dependent change of UV spectrum after a solution containing Comparative Compound 1 was exposed to UVA.
Figure 3:
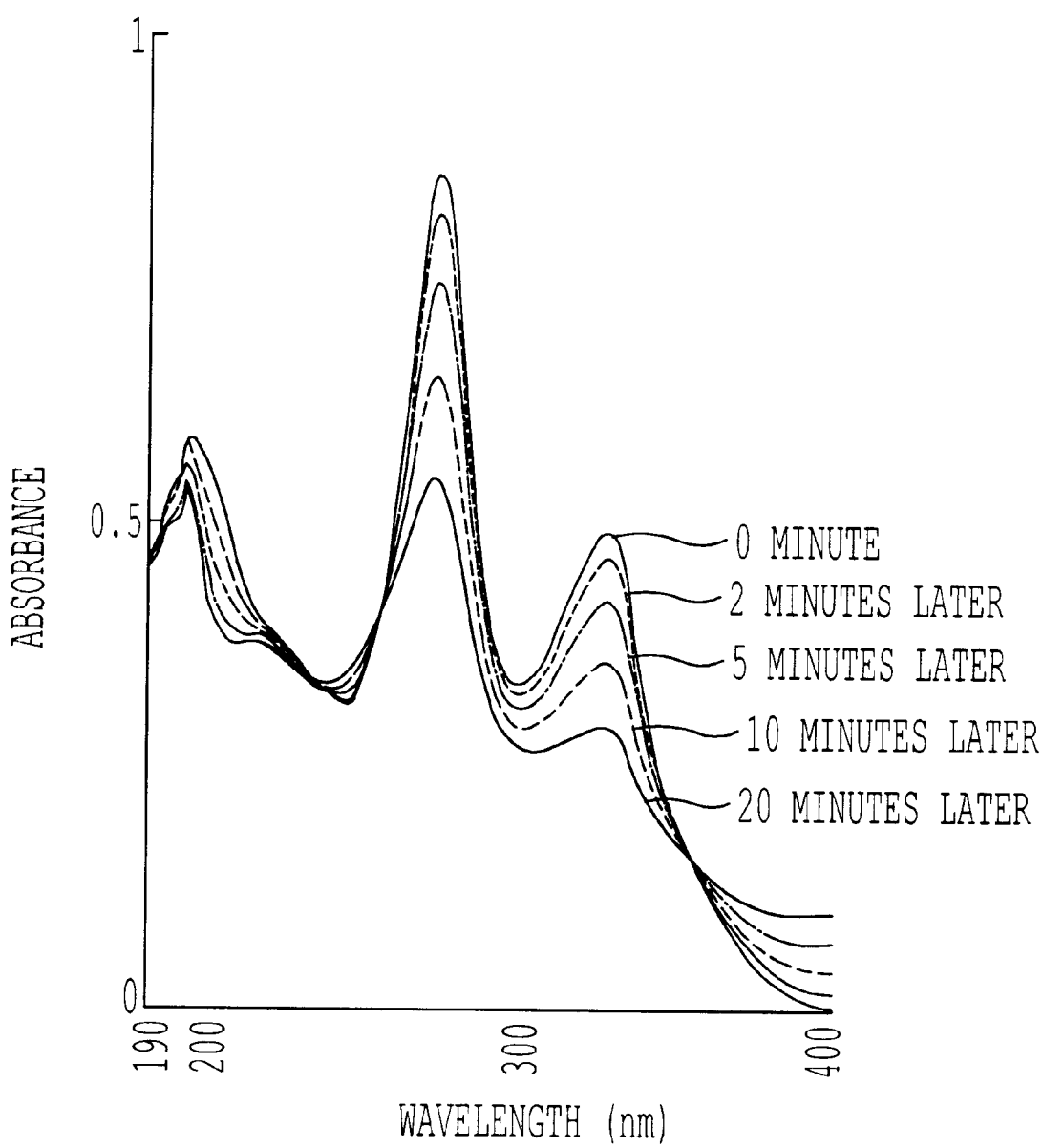
FIG. 3 shows a time-dependent change of UV spectrum after a solution containing Comparative Compound 2 was exposed to UVA.

It is widely disclosed in WO97/11068 that quinolinecarboxylic acids having a 6-amino-3,5-difluoropyidinyl group on position 1 are antibacterial agents having excellent antibacterial action as well as low toxicity. Among them, those having a hydroxyazetidinyl group on position 7 are so-called acidic quinolone compounds. Since they exhibit efficacy against bacteria at the inflammatory site which tend to have reduced pH in a living body environment, bacteria englobed by a macrophage or neutrophil, intracellular parasitic bacteria and the like, they are presumed to be particularly useful when clinically applied. The acidic quinolone compounds, which have so far been found, however show an undesirable tendency to be decomposed in a relatively short time in an aqueous solution by exposure to ultraviolet rays (FIGS. 2 and 3).

It is an utterly unexpected fact that the invention compound having a methyl group introduced on position 8 is hardly decomposed by exposure to light for long hours, thus exhibiting high photostability (FIG. 1) and at the same time, it has all the excellent properties which compounds of the similar series possess (Tests (1) and (2)).

The compounds of the present invention can each be converted into both acid addition salts and base addition salts. Incidentally, these salts include those formed into chelate salts with a boron compound.

Examples of the acid addition salt include (i) salts with a mineral acid such as hydrochloric acid or sulfuric acid, (ii) salts with an organic carboxylic acid such as formic acid, citric acid, trichloroacetic acid, trifluoroacetic acid, fumaric acid or maleic acid, and (iii) salts with a sulfonic acid such as methanesulfonic acid, benzenesulfonic acid, p-toluenesulfonic acid, mesitylenesulfonic acid or naphthalenesulfonic acid. Examples of the base addition salt include (i') salts with an alkali metal such as sodium or potassium, (ii') salts with an alkaline earth metal such as calcium or magnesium, (iii') ammonium salt, (iv) salts with a nitrogen-containing organic base such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine or N,N'-dibenzylethylenediamine. Examples of the boron compound include boron halides such as boron fluoride and lower acyloxy borons such as acetoxy boron.

The compounds or salts thereof can exist not only in unsolvated forms but also in hydrated or solvated forms. Accordingly, the compounds of the present invention embrace those in any crystalline form, and hydrated and solvated forms.

The compounds or salts thereof are prepared by any desired process. The following is one example of it.

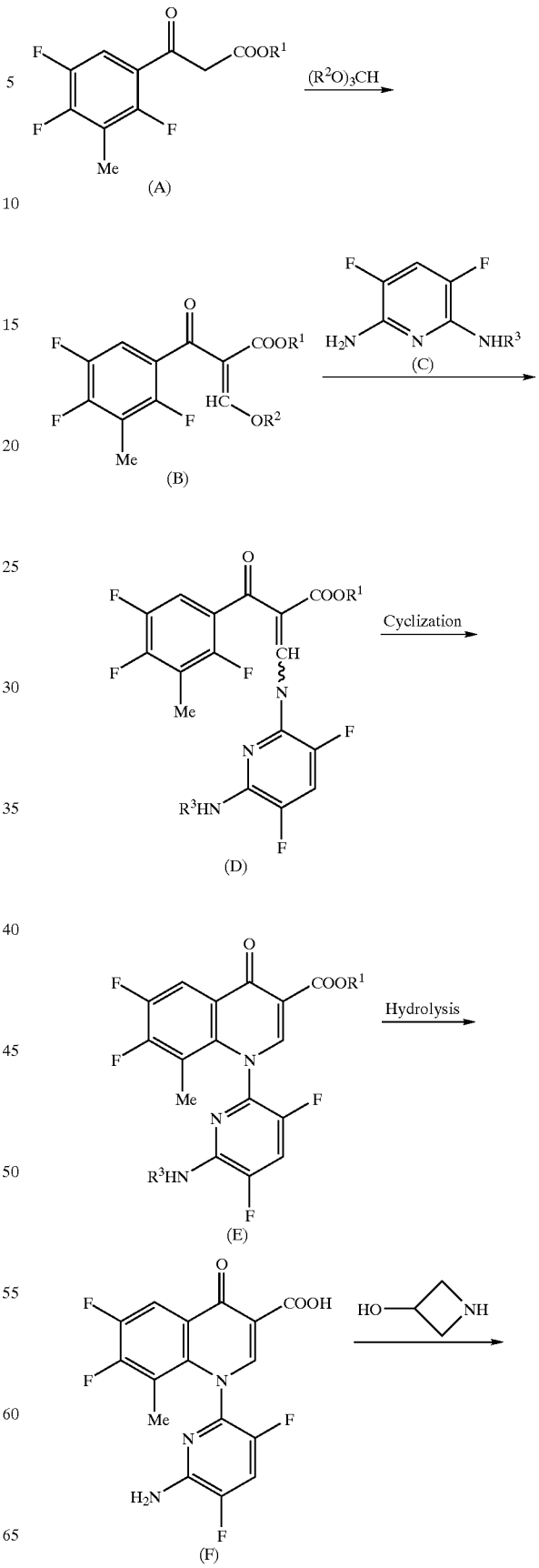

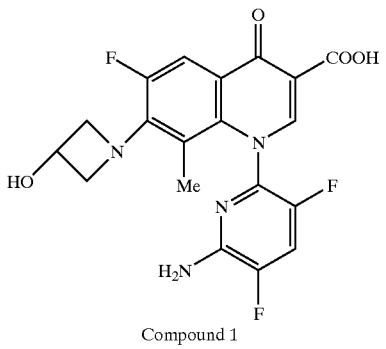

Compound 1

[wherein, $R^1$ and $R^2$ each represents a lower alkyl group and $R^3$ represents a hydrogen atom or an amino protective group].

Invention compound 1 can be prepared by reacting Compound (A) with an orthoformate such as ethyl orthoformate or methyl orthoformate to produce Acrylate derivative (B), reacting the acrylate derivative with Amino compound (C) into Compound (D), cyclizing the resulting compound to produce compound (E), hydrolyzing the resulting compound into compound (F) and then reacting the resulting compound with 3-hydroxyazetidine.

Examples of the lower alkyl group represented by $R^1$ or $R^2$ include $C_{1-4}$ alkyl groups such as methyl, ethyl, propyl and butyl. Examples of the amino protective group represented by $R^3$ include t-butylamino, benzyl, p-methoxybenzyl and 1,1,3,3-tetramethylbutyl groups.

Compound (A) and an orthoformate are usually reacted at 0 to 160° C., preferably at 50 to 150° C., and the reaction time usually ranges from 10 minutes to 48 hours, preferably from 1 to 10 hours. The orthoformate is used in at least an equimolar amount, more preferably, in a molar amount about 1 to 10 times, both relative to Compound (A). As a reaction assistant, addition of a carboxylic anhydride such as acetic anhydride is desired. The reaction assistant is added in an amount of at least an equimolar amount, more preferably, in a molar amount about 1 to 10 times, both relative to Compound (A).

The reaction with Compound (C) is carried out in a proper solvent or in a solventless manner. Any solvent inert to the reaction can be used and examples include aromatic hydrocarbons such as benzene, toluene and xylene, ethers such as diethyl ether, tetrahydrofuran, dioxane, monoglyme and diglyme, aliphatic hydrocarbons such as pentane, hexane, heptane and ligroin, halogenated hydrocarbons such as methylene chloride, chloroform and carbon tetrachloride, aprotic polar solvents such as dimethylformamide and dimethylsulfoxide, and alcohols such as methanol, ethanol and propanol. This reaction is usually carried out at 0 to 150° C., preferably 0 to 100° C. and the reaction time usually ranges from 10 minutes to 48 hours. Compound (C) is used in at least an equimolar amount, preferably in a molar amount 1 to 2 times, both relative to Compound (B).

Alternatively, Compound (D) can be obtained by reacting Compound (A) with an acetal such as N,N-dimethylformamide dimethylacetal or N,N-dimethylformamide diethylacetal and then reacting the reaction mixture with Compound (C). Any solvent inert to this reaction can be used for the reaction with an acetal. For example, the above-exemplified ones can be employed. The reaction is usually effected at 0 to 150° C., preferably at room temperature to 100° C. and the reaction time ranges from 10 minutes to 48 hours, preferably 1 to 10 hours.

The reaction to obtain Compound (E) by subjecting Compound (D) to cyclization is carried out in a proper solvent in the presence or absence of a basic compound. Any solvent inert to the reaction can be used for this reaction. Examples include aromatic hydrocarbons such as benzene, toluene and xylene, ethers such as diethyl ether, tetrahydrofuran, dioxane, monoglyme and diglyme, halogenated hydrocarbons such as methylene chloride, chloroform and carbon tetrachloride, dipolar aprotic solvents such as dimethylformamide and dimethylsulfoxide, and alcohols such as methanol, ethanol and propanol. Examples of the basic compound include alkali metals such as metal sodium and metal potassium, metal hydrides such as sodium hydride and calcium hydride, inorganic salts such as sodium hydroxide, potassium hydroxide, sodium carbonate and potassium carbonate, alkoxides such as sodium methoxide, sodium ethoxide and potassium-t-butoxide, metal fluorides such as sodium fluoride and potassium fluoride, and organic bases such as trimethylamine, 1,8-diazabicyclo[5.4.0]undecene (DBU).

This reaction is usually effected at 0 to 200° C., preferably at room temperature to 180° C. and the reaction is usually completed in 5 minutes to 24 hours. The basic compound is used in at least an equimolar amount, preferably in a molar amount 1 to 2 times, both relative to Compound (D).

Compound (F) can be obtained by hydrolyzing Compound (E), thereby eliminating the carboxy protective group of $R^1$ and/or amino protective group of $R^3$.

The hydrolysis can be carried out under any reaction condition used for usual hydrolysis. It is, for example, conducted in the presence of a basic compound such as sodium hydroxide, potassium hydroxide, sodium carbonate or potassium carbonate, a mineral acid such as hydrochloric acid, sulfuric acid or hydrobromic acid, or an organic acid such as p-toluenesulfonic acid, in a solvent, for example, water, an alcohol such as methanol, ethanol or propanol, an ether such as tetrahydrofuran or dioxane, a ketone such as acetone or methyl ethyl ketone, or acetic acid, or a mixed solvent thereof. This reaction is usually carried out at room temperature to 180° C., preferably at room temperature to 140° C. and the reaction time usually ranges from 1 to 24 hours.

Then, Compound (F) is reacted with 3-hydroxyazetidine or acid addition salt thereof to obtain Invention compound 1.

This reaction is carried out in a solvent inert to the reaction, for example, an aromatic hydrocarbon such as benzene, toluene or xylene, an alcohol such as methanol or ethanol, an ether such as tetrahydrofuran, dioxane or monoglyme, a halogenated hydrocarbon such as methylene chloride, chloroform or carbon tetrachloride, a aprotic polar solvent such as dimethylformamide, dimethylsulfoxide or N-methylpyrrolidone, acetonitrile or pyridine, optionally in the presence of a deacidifying agent such as sodium carbonate, calcium carbonate, triethylamine or 1,8-diazabicyclo[5.4.0]undecene (DBU) at room temperature to 160° C. The reaction time ranges from several minutes to 48 hours, preferably 10 minutes to 24 hours. 3-Hydroxyazetidine is preferably added in at least an equimolar amount, more preferably, in a molar amount 1 to 5 times, both relative to Compound (F).

Compound 1 can be converted into a corresponding acid addition salt or base addition salt in a conventional manner, for example, by the method described below.

Specifically, the conversion is carried out by treating Invention compound 1 at room temperature or under heat as desired in the presence of a mineral acid such as hydrochloric acid or sulfuric acid, an organic carboxylic acid such as formic acid, citric acid, trichloroacetic acid, trifluoroacetic acid, fumaric acid or maleic acid, a sulfonic acid such as methanesulfonic acid, benzenesulfonic acid, p-toluenesulfonic acid, mesitylenesulfonic acid or naphthalenesulfonic acid, a basic compound such as sodium hydroxide, potassium hydroxide, calcium hydroxide or magnesium hydroxide or a nitrogen-containing organic base such as ammonium, trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-efenamine or N,N'-dibenzylethylenediamine in a polar solvent, for example, an alcohol such as methanol or ethanol or water.

Incidentally, the starting compound (A) can be prepared by any one of the processes described in the below-described documents or by a similar process.

(1) J. Heterocyclic Chem. 22, 1033(1985)
(2) Liebigs Ann. Chem. 29(1987)
(3) J. Med. Chem. 31, 991(1988)
(4) J. Org. Chem. 35, 930(1970)
(5) Japanese Patent Application Laid-Open No. Sho 62-246541
(6) Japanese Patent Application Laid-Open No. Sho 62-26272
(7) Japanese Patent Application Laid-Open No. Sho 63-145268
(8) J. Med. Chem. 29, 2363(1986)
(9) J. Fluorin. Chem. 28, 361(1985)
(10) Japanese Patent Application Laid-Open No. Sho 63-198664
(11) Japanese Patent Application Laid-Open No. Sho 63-264461
(12) Japanese Patent Application Laid-Open No. Sho 63-104974
(13) European Patent Application No. 230948
(14) Japanese Patent Application Laid-Open No. Hei 2-282384
(15) Japanese Language Laid-Open Publication (PCT) No. Hei 3-502452
(16) J. Heterocyclic Chem. 27, 1609(1990)
(17) Japanese Patent Application Laid-Open No. Hei 7-215913
(18) WO97/40036

The starting compound (C) can be prepared in any desired process. It may be prepared, for example, by a substituting the halogen atom, which has been bonded to the carbon atom constituting the 6-membered ring, with an amine derivative, for example, in accordance with a known halogen-amine substitution reaction as described in WO97/11068 or WO97/38971.

The invention compound thus obtained can be isolated and purified in a conventional manner and it is available in the form of a salt or a free carboxylic acid, depending on the isolation and purification conditions. The form of the compound, however, may be converted into another form, and thus, the compound of the present invention can be prepared in a desired form.

Although the compound or salt thereof thus obtained is an acidic quinolone compound, it has excellent photostability so as to substantially prevent decomposition even by exposure to light for long hours, while sustaining excellent antibacterial activity and excellent properties free from side effects such as phototoxicity which are inherent to pyridonecarboxylic acid derivatives represented by the formula (I).

The compound or salt thereof according to the present invention may be formulated into an antibacterial composition with a pharmaceutically acceptable carrier for parenteral administration such as injection, rectal administration or ophthalmic administration, or oral administration in the solid or liquid form.

Preparations of the present invention for use as injections can take the form of pharmaceutically acceptable germ-free aqueous solutions, nonaqueous solutions, suspensions or emulsions. Examples of the suitable non-aqueous carrier, diluent, solvent or vehicle include propylene glycol, polyethylene glycol, vegetable oils such as olive oil and injectable organic esters such as ethyl oleate. In such a solution, an adjuvant such as antiseptic, humectant, emulsifier or dispersant can be incorporated as needed. These injections can be sterilized, for example, by filtering them through a bacterial filter or by mixing, immediately before use, a sterilizing agent or a sterilizing agent in the form of a germ-free solid composition soluble in some other sterilizable and injectable media.

Preparations for ophthalmic administration may each preferably contain, in addition to the invention compound, a solubilizing agent, preservative, isotonic agent, thicker and the like as needed.

Examples of the orally administrable solid preparation include capsules, tablets, pills, powders and granules. Upon formulation of such a solid preparation, the compound according to the present invention is mixed with at least one inert diluent such as sucrose, lactose or starch. Upon usual formulation, one or more substances other than the inert diluent, for example, a lubricant (e.g., magnesium stearate) can also be incorporated in the preparation. A buffer can also be incorporated in capsules, tablets or pills, whereas enteric coating may be applied to tablets or pills.

Examples of the orally administrable liquid preparation include ordinarily employed inert diluents such as, in addition to water, pharmaceutically acceptable emulsions, solutions, suspending agents, syrups and elixirs. In addition to such an inert diluent, adjuvants such as sweetening agent, seasoning agent and flavor as well as humectant, emulsifier and suspending agent may be incorporated.

The transrectally administrable preparations may contain, in addition to the invention compound, an excipient such as cacao butter or suppository wax as needed.

Although the dosage of the invention compound varies depending on the properties of the compound, administration route, desired treatment term and other factors, the compound is generally administered in an amount of about 0.1 to 1000 mg/kg a day, with about 0.5 to 100 mg/kg being particularly preferred. If desired, this daily dosage may be administered in 2 to 4 portions.

EXAMPLES present invention will hereinafter be described more specifically by the following examples and referential examples.

Referential Example 1

Synthesis of ethyl 1-(6-t-butylamino-3,5-difluoropyridin-2-yl)-6,7-difluoro-8-methyl-1,4-dihydro-4-oxoquinoline-3-carboxylate To 3.4 g of ethyl 2,4,5-trifluoro-3-methylbenzoylacetate were added 3.2 g of acetic anhydride and 2.3 g of triethyl orthoformate, followed by heating under reflux for 4 hours. After removal of the solvent by distillation, toluene was added to the residue for azeotropic distillation. To the residue was added 5 ml of ethanol. At 0° C., a solution of 2.7 g of 2-amino-6-t-butylamino-3,5-difluoropyridine dissolved in 20 ml of ethanol was added dropwise, followed by stirring at room temperature for 20 minutes. The reaction mixture was distilled to remove the solvent and the residue was subjected to chromatography on a silica gel column. From the eluate fraction of ethyl acetate-hexane=1:8, 4.6 g of ethyl 2-(2,4,5-trifluoro-3-methylbenzoyl)-3-(6-t-butylamino-3,5-difluoropyridin-2-yl)aminoacrylate was obtained as an oil. To a solution of 4.6 g of the resulting ethyl 2-(2,4,5-trifluoro-3-methylbenzoyl)-3-(6-(t-butylamino-3,5-difluoropyridin-2-yl)aminoacrylate in 10 mL of N,N-dimethylformamide, was added 1.4 g of potassium carbonate, followed by stirring at 100° C. for 50 minutes. Water and ethyl acetate were added to the reaction mixture for extraction. The organic layer was then separated from the extract, dried over magnesium sulfate and distilled to remove the solvent. The residue was collected by filtration using ethanol and then washed with diethyl ether, whereby 2.6 g of the title compound was obtained as a pale yellow powder.

Melting point: 207 to 211° C.

$^1$HNMR (d$_6$-DMSO) δ; 1.34–1.48(m,12H), 1.82(d,J=3 Hz,3H), 4.40(q,J=7 Hz,2H), 4.75(brs,1H), 7.23(t, J=9 Hz,1H), 8.22(t,J=10 Hz,1H), 8.50(s,1H).

Referential Example 2

Synthesis of 1-(6-amino-3,5-difluoropyridin-2-yl)-6,7-difluoro-8-methyl-1,4-dihydro-4-oxoquinoline-3-carboxylic acid To 2.5 g of ethyl 1-(6-t-butylamino-3,5-difluoropyridin-2-yl)-6,7-difluoro-8-methyl-1,4-dihydro-4-oxoquinoline-3-carboxylate was added 10 mL of 36% hydrochloric acid, followed by heating under reflux overnight. After the reaction mixture was allowed to cool down, the resulting precipitate was collected by filtration. The precipitate was washed with ethanol and then with diethyl ether, whereby 1.7 g of the title compound was obtained as a pale yellow powder.

Melting point: 274 to 277° C.

$^1$HNMR (d$_6$-DMSO) δ; 1.84(s,3H), 6.91(brs,2H), 8.03(t, J=9 Hz,1H), 8.25(t,J=9 Hz,1H), 8.93(s,1H).

Example 1

Synthesis of 1-(6-amino-3,5-difluoropyridin-2-yl)-6-fluoro-7-(3-hydroxyazetidin-1-yl)-8-methyl-1,4-dihydro-4-oxoquinoline-3-carboxylic acid To 5 mL of dimethylsulfoxide were added 1.8 g of 1-(6-amino-3,5-difluoropyridin-2-yl)-6,7-difluoro-8-methyl-1,4-dihydro-4-oxoquinoline-3-carboxylic acid, 1.1 g of 3-hydroxyazetidine.hydrochloride, 0.6 g of lithium hydroxide and 0.2 g of magnesium chloride, followed by stirring at room temperature for 21 hours. The reaction mixture was added to 60 mL of a 10% aqueous solution of citric acid while stirring. The precipitate was collected by filtration and then washed with water. The solid thus obtained was dispersed in 20 mL of ethanol, followed by heating under reflux for 15 minutes. The pale yellow precipitate was collected by filtration and washed with ethanol. The solid thus obtained was dissolved in 10 mL of pyridine and the resulting solution was concentrated under reduced pressure. The precipitate was collected by filtration and washed with ethanol, whereby 1.3 g of the title compound in the form of a pyridine complex was obtained as a pale yellow powder (melting point: 244 to 247° C.).

The resulting pyridine complex was dispersed in 50 mL of distilled water, followed by heating under reflux for 20 minutes. The precipitate was collected by filtration, washed with distilled water and dried over phosphorus pentaoxide under reduced pressure, whereby 1.1 g of the title compound was obtained.

Melting point: 245 to 247° C.

$^1$HNMR (d$_6$-DMSO) δ; 1.64(s,3H), 3.94(m,1H), 4.03(m, 1H), 4.49(m,3H), 5.69(d,J=5 Hz,1H), 6.85(brs,2H), 7.77(d, J=14 Hz,1H), 7.96(t,J=10 Hz,1H), 8.72(s,1H)

Tests

The compounds according to the present invention were tested for their antibacterial action, phototoxicity and photostability. The results will be described below in (1) to (3). For comparison, used were 1-(6-amino-3,5-difluoropyridin-2-yl)-8-chloro-6-fluoro-7-(3-hydroxyazetidin-1-yl)-1,4-dihydro-4-oxoquinoline-3-carboxylic acid.3-hydroxyazetidine salt (Comparative compound 1), 1-(6-amino-3,5-difluoropyridin-2-yl)-6,8-difluoro-7-(3-hydroxyzetidin-1-yl)-1,4-dihydro-4-oxoquinoline-3-carboxylic acid (Comparative compound 2) and commercially available 1-cyclopropyl-6-fluoro-7-(1-piperazinyl)-1,4-dihydro-4-oxoquinoline-3-carboxylic acid (ciprofloxacin), S-(–)-9-fluoro-2,3-dihydro-3-methyl-10-(4-methyl-1-piperazinyl)-7-oxo-7H-pyrido[1,2,3-de][1,4]-benzoxazine-6-carboxylic acid (levofloxacin), (±)-7-(3-amino-1-pyrrolidinyl)-6-fluoro-1-(2,4-difluorophenyl)-1,4-dihydro-4-oxo-1,8-naphthyridine-3-carboxylic acid (tosufloxacin) and 7-([1α, 5α, 6α]-6-amino-3-azabicyclo[3.1.0]hex-1-yl)-6-fluoro-1-(2,4-difluorophenyl)-1,4-dihydro-4-oxo-1,8-naphthyridine-3-carboxylic acid (trovafloxacin).

(1) Test on Antibacterial Action

In accordance with the standard method established by Japan Society of Chemotherapy (CHEMOTHERAPY, 29(1),76(1981)), the minimum growth inhibitory concentration (MIC: μg/mL) was measured. The results are shown in Table 1.

TABLE 1

| | Compound 1 | Comparative compound 1 | Comparative compound 2 | Ciprofloxacin | Levofloxacin |
| --- | --- | --- | --- | --- | --- |
| S. aureus 209P | 0.006 | 0.006 | 0.013 | 0.20 | 0.20 |
| S. aureus Smith | <0.003 | 0.003 | 0.006 | 0.20 | 0.10 |
| MRSA W200 | 0.013 | 0.006 | 0.025 | 0.78 | 0.39 |
| S. epidermidis IFO12293 | 0.013 | 0.013 | 0.050 | 0.78 | 0.39 |
| B. subtilis ATCC6633 | 0.025 | 0.05 | 0.025 | 0.05 | 0.10 |
| E. coli NIHJ-JC2 | 0.05 | 0.05 | 0.10 | 0.013 | 0.05 |
| K. peumoniae KC-1 | 0.05 | 0.05 | 0.10 | 0.025 | 0.05 |
| P. aeruginosa IFO3445 | 0.39 | 0.39 | 0.39 | 0.39 | 0.78 |

(2) Test on Phototoxicity

The phototoxicity was tested in accordance with the following method.

After intravenous administration (40 mg/kg/10 mL) of each of the test compounds to a female ICR mouse (5–6 week old), the mouse was exposed to ultraviolet rays (320 to 400 nm, 1.8 mW/cm$^2$/sec) for 4 hours. Its ears were observed for any abnormality after an elapse of each of 24 and 48 hours, with the time rightly after exposure being designated as 0 hour, and evaluated based on the below-described criteria. The average score was calculated and results are shown in Table 2.

no abnormality (0 point); slight erythema (1 point); medium erythema (2 points); and heavy erythema or edema (3 points)

TABLE 2

| | Scores (frequency) | | |
|---|---|---|---|
| | 0 hour | 24 hours | 48 hours |
| Compound 1 | 0 (0/4) | 0 (0/4) | 0 (0/4) |
| Comparative compound 1 | 0 (0/4) | 0 (0/4) | 0 (0/4) |
| Comparative compound 2 | 0 (0/4) | 0 (0/4) | 0 (0/4) |
| Tosufloxacin | 1.8 (4/5) | 0.8 (4/5) | 0.2 (1/5) |
| Trovafloxacin | 1.5 (4/4) | 0 (0/4) | 0 (0/4) |

(2) Test on Photostability

The test on photostability was made in accordance with the following method.

Figure 1:
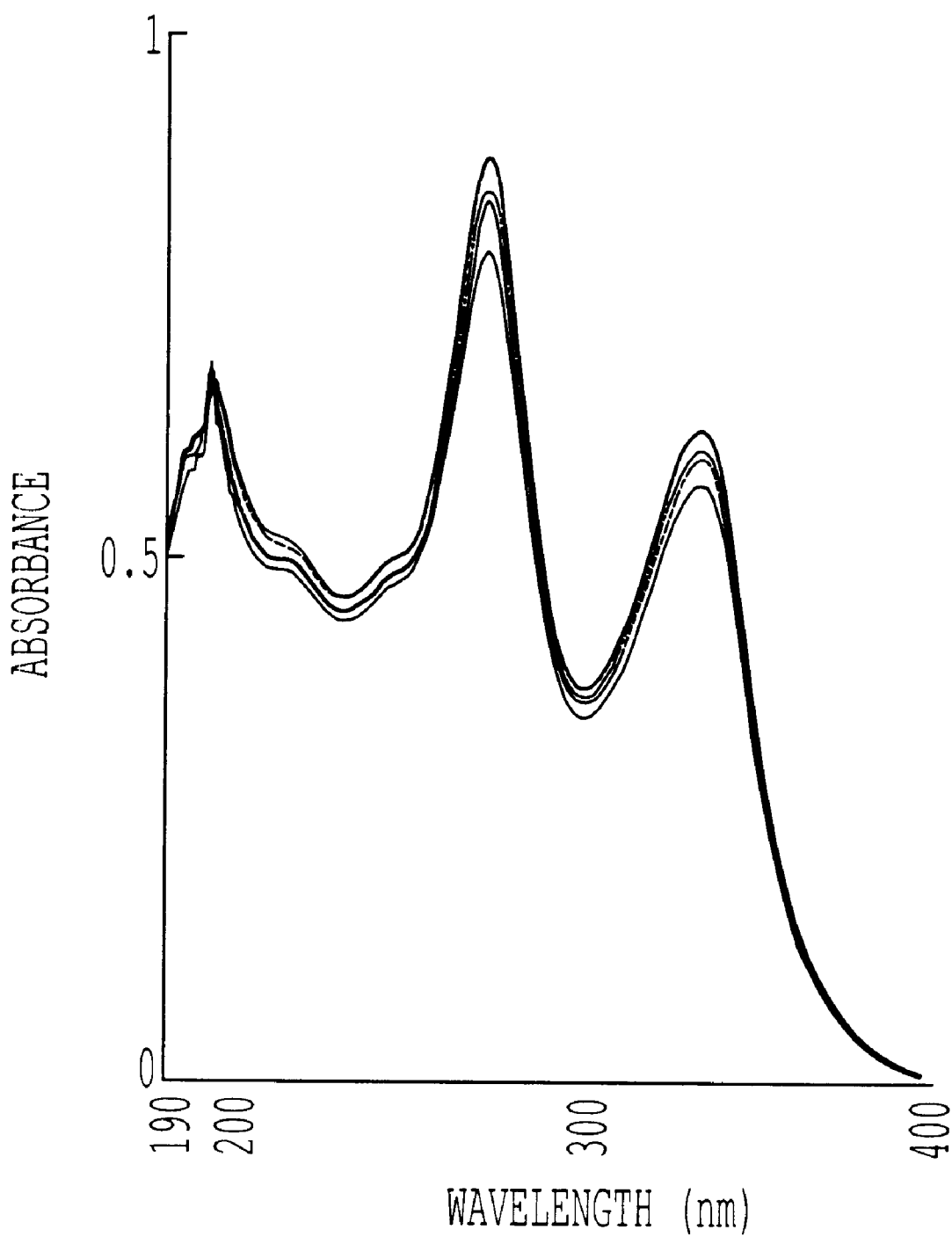
FIG. 1 shows a time-dependent change of UV spectrum after a solution containing Compound 1 was exposed to UVA.

With 0.08% NaOH, 1 mg/mL of the test compound was prepared. The resulting solution was diluted 100-fold with PBS(−). Into the wells of a 24-well plate, 1.5 ml portions of the diluted solution were poured, respectively. Just after the solution was exposed to UVA under an UV light (black light, product of Toshiba Corporation) for 0, 2, 5, 10 and 20 minutes, UV spectra within a range of 190 to 400 nm were measured ("UV-240", product of Shimadzu Corporation). The results are shown in FIGS. 1 to 3.

The above-described results demonstrate that the invention compound was hardly decomposed by exposure to ultraviolet rays for 20 minutes.

Formulation Example 1 (Tablets)

To Compound 1 were added lactose, corn starch, crystalline cellulose, carmellose calcium and magnesium stearate in accordance with the formulation amounts as shown in Table 3, respectively, followed by mixing for 15 minutes in a Bohle container mixer (manufactured by Kotobuki Engineering & Manufacturing Corp. Ltd.). The resulting powders were compression-molded by a tableting machine ("CORRECT 19K", manufactured by Kikusui Seisakusho, Ltd.), whereby tablets having a diameter of 8 mm and weight of 250 mg were obtained. The resulting tablets were found to have excellent hardness and intragastric desintegration.

TABLE 3

| Component | weight % |
|---|---|
| Compound 1 | 40 |
| Lactose | 24 |
| Corn starch | 17 |

TABLE 3-continued

| Component | weight % |
|---|---|
| Crystalline cellulose | 12 |
| Carmellose calcium | 6 |
| Magnesium stearate | 1 |
| Total | 100 |

Formulation Example 2 (Injection)

To Compound 1 were added 2 g of glycerin (solubilizing assistant), polysorbate 80 (solubilizing agent) and distilled water for injection to dissolve the former in the latter. To the resulting solution were added a buffer and sodium chloride (isotonic agent), whereby 300 mL of an isotonic solution having pH 6.0 was obtained. The resulting solution was filtered through a membrane filter of 0.22 μm. A sterilized vial was filled with 30 ml of the filtrate, whereby an injection was prepared.

Formulation Example 3 (Ointment)

To 90 g of a hydrophilic plastibase was added 1 g of Compound 1, followed by uniform dispersion. To the resulting dispersion were added 3 g of light silicic anhydride and 6 g of octadodecyl myristate and the resulting mixture was kneaded for 20 minutes. An aluminum tube was filled with 10 g of the kneaded mass, whereby an ointment containing 1% of Compound 1 was obtained.

Formulation Example 4 (Eye Drop)

In 100 mL of sterilized and purified water was dissolved 0.3 g of Compound 1, followed by the addition of a buffer and sodium chloride, whereby an isotonic solution of pH 7.5 was obtained. A sterilized container was filled with 5 mL of the resulting solution, whereby an eye drop containing 0.3% of Compound 1 was obtained.

INDUSTRIAL APPLICABILITY

The compounds or salts thereof according to the present invention exhibit markedly stable light stability, while maintaining excellent antibacterial activity and excellent phototoxicity-free properties which are inherent to quinolone-base antibacterial agents. Antibacterial agents comprising, as an active ingredient, the invention compound or salt thereof can be stored over a long period of time without suffering from any decrease in the drug effect, can be supplied as stable preparations even in the dosage form of an injection, eye drop or surgical medicine without any pharmaceutical device against exposure to light and can be used widely not only as pharmaceuticals for human beings and animals but also as medicines for fishes, agricultural chemicals or food preservatives.

What is claimed is:

1. A 1-(6-amino-3,5-difluoropyridin-2-yl)-6-fluoro-7-(3-hydroxyazetidin-1-yl)-8-methyl-1,4-dihydro-4-oxoquinoline-3-carboxylic acid or a salt thereof.

2. A pharmaceutical composition comprising a 1-(6-amino-3,5-difluoropyridin-2-yl)-6-fluoro-7-(3-hydroxyazetidin-1-yl)-8-methyl-1,4-dihydro-4-oxoquinoline-3-carboxylic acid or a salt thereof, and a pharmaceutically acceptable carrier.

3. A pharmaceutical composition of claim 2, which is an antibacterial composition.

4. A method for treating infectious diseases, which comprises administering to an individual in need thereof a 1-(6-amino-3,5-difluoropyridin-2-yl)-6-fluoro-7-(3-hydroxyazetidin-1-yl)-8-methyl-1,4-dihydro-4-oxoquinoline-3-carboxylic acid or a salt thereof.

5. The pharmaceutical composition of claim 2, Which is a solid composition.

6. The pharmaceutical composition of claim 2, which is a liquid composition.

7. The method of claim 4, wherein the compound is administered parenterally.

8. The method of claim 4, wherein the compound is administered orally.

9. The method of claim 4, wherein the compound is administered in an amount of 0.1 to 1000 mg/kg per day.

10. The method of claim 4, wherein the compound is administered in an amount of 0.5 to 100 mg/kg per day.

11. A method of treating a bacterial infection in an individual, comprising administering the compound of claim 1 to the individual in an amount to treat the bacterial infection.

12. The method of claim 11, wherein the compound is administered parenterally.

13. The method of claim 11, wherein the compound is administered orally.

14. The method of claim 11, wherein the compound is administered in an amount of 0.1 to 1000 mg/kg per day.

15. The method of claim 11, wherein the compound is administered in an amount of 0.5 to 100 mg/kg per day.

\* \* \* \* \*